United States Patent
Cheng et al.

(10) Patent No.: US 11,448,675 B2
(45) Date of Patent: Sep. 20, 2022

(54) CAPACITANCE DETECTION MODULE, METHOD AND ELECTRONIC DEVICE

(71) Applicant: SHENZHEN GOODIX TECHNOLOGY CO., LTD., Shenzhen (CN)

(72) Inventors: Shuqing Cheng, Shenzhen (CN); Ming Yang, Shenzhen (CN); Fulin Li, Shenzhen (CN); Zicheng Guo, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 372 days.

(21) Appl. No.: 16/700,967

(22) Filed: Dec. 2, 2019

(65) Prior Publication Data

US 2020/0103446 A1 Apr. 2, 2020

Related U.S. Application Data

(63) Continuation of application No. PCT/CN2018/109204, filed on Sep. 30, 2018.

(51) Int. Cl.
| | |
|---|---|
| *G01R 27/26* | (2006.01) |
| *A61B 5/00* | (2006.01) |
| *H03K 17/96* | (2006.01) |

(52) U.S. Cl.
CPC ........ *G01R 27/2605* (2013.01); *A61B 5/6802* (2013.01); *H03K 17/962* (2013.01); *H03K 17/96* (2013.01)

(58) Field of Classification Search
CPC ........ G01R 27/00; G01R 27/02; G01R 27/26; G01R 27/2605; G01D 5/00; G01D 5/12;
(Continued)

(56) References Cited

U.S. PATENT DOCUMENTS

| 7,782,220 B2 * | 8/2010 | Nakamura | ........... H03K 17/955 |
| | | | 340/545.4 |
| 2008/0246723 A1 * | 10/2008 | Baumbach | ............ G06F 3/0443 |
| | | | 345/156 |

(Continued)

FOREIGN PATENT DOCUMENTS

| CN | 101078774 A | 11/2007 |
| CN | 101882038 A | 11/2010 |

(Continued)

OTHER PUBLICATIONS

European Search Report.
(Continued)

*Primary Examiner* — Hoai-An D. Nguyen

(74) *Attorney, Agent, or Firm* — J.C. Patents

(57) ABSTRACT

The present application provides a capacitance detection module, a method and an electronic device, including: a sensing module and detecting circuit; a first sensing unit is disposed on the first surface of the sensing module, and a second sensing unit is disposed on the second surface of the sensing module; the first sensing unit and the second sensing unit are respectively connected to the detecting circuit; the detecting circuit is configured to determine, according to the capacitance value of the first sensing unit and the capacitance value of the second sensing unit, the wearing state of the user to the device having the capacitance detection module. Thereby the problem that the capacitance detection is affected by temperature is avoided.

6 Claims, 13 Drawing Sheets

Capacitance detection module 70

(58) Field of Classification Search
CPC ... G01D 5/14; G01D 5/24; A61B 5/00; A61B 5/68; A61B 5/6801; A61B 5/6802; A61B 5/6803; A61B 5/6813; A61B 5/6814; A61B 5/6815; A61B 5/6843; A61B 2562/00; A61B 2562/02; A61B 2562/0209; A61B 2562/0214; H03K 17/00; H03K 17/94; H03K 17/96; H03K 17/962; H03K 2217/00; H03K 2217/94; H03K 2217/96; H03K 2217/9607; H03K 2217/960705; H03K 2217/960735; H03K 2217/960745
USPC ...... 324/600, 649, 658, 679, 686; 702/1, 47, 702/52
See application file for complete search history.

(56) References Cited

U.S. PATENT DOCUMENTS

| | | |
|---|---|---|
| 2010/0230181 A1 | 9/2010 | Suzuki |
| 2014/0239982 A1 | 8/2014 | Alameh et al. |
| 2018/0014787 A1 | 1/2018 | Ganton et al. |
| 2018/0300005 A1* | 10/2018 | Yeo ..................... B32B 25/045 |

FOREIGN PATENT DOCUMENTS

| | | | |
|---|---|---|---|
| CN | 105581411 A | * | 5/2016 |
| CN | 106054273 A | | 10/2016 |
| CN | 205809842 U | | 12/2016 |
| CN | 107065016 A | | 8/2017 |
| CN | 107463289 A | | 12/2017 |
| CN | 107515692 A | | 12/2017 |
| CN | 107636596 A | | 1/2018 |
| CN | 107907916 A | | 4/2018 |
| CN | 107949824 A | | 4/2018 |
| EP | 1860776 A2 | | 11/2007 |
| JP | 2004-022356 A | | 1/2004 |
| JP | 2007-157371 A | | 6/2007 |
| JP | 2007-208682 A | | 8/2007 |
| JP | 2010-217967 A | | 9/2010 |
| JP | 2012-503831 A | | 2/2012 |
| JP | 2018-060502 A | | 4/2018 |
| JP | 2018-120757 A | | 8/2018 |

OTHER PUBLICATIONS

The first Office Action of the parallel CN application.
The International Search Report of corresponding International application No. PCT/CN2018/109204, dated Jun. 28, 2019.
The Japanese Examination Report of corresponding Japanese application No. 2019-508199, dated Oct. 1, 2019.

* cited by examiner

CAPACITANCE DETECTION MODULE, METHOD AND ELECTRONIC DEVICE

CROSS-REFERENCE TO RELATED APPLICATIONS

This application is a continuation of the International Application No. PCT/CN2018/109204, filed on Sep. 30, 2018, entitled "CAPACITANCE DETECTION MODULE, METHOD AND ELECTRONIC DEVICE", the content of which is incorporated herein by reference in its entirety.

TECHNICAL FIELD

The present application relates to the field of capacitance detection technology and, in particular, to a capacitance detection module, a method and an electronic device.

BACKGROUND

With the development of technology, electronic devices are becoming more and more intelligent. For example, there is a kind of earphone in the market, when a user puts the earphone into the ear or removes the earphone, the earphone can automatically sense, that is, when the user puts the earphone, music could be played automatically, and the music could be paused when the user removes the earphone. This detecting principle could be implemented based on a capacitance detection module.

Specifically, FIG. 1 is a schematic diagram of a capacitance detection module 10 provided by the prior art. As shown in FIG. 1, the capacitance detection module 10 includes: a sensing module 11 (which may be a flexible printed circuit board (FPC)) and a detecting circuit 12. The upper surface of the sensing module 11 is provided with a sensor 13, the lower surface of the sensing module 11 is provided with a ground unit (GND) 14, and a dielectric layer 15 could be disposed between the sensor 13 and the ground unit (GND) 14. When a human body approaches the sensor 13, an electric field between the sensor 13 and the ground unit 14 changes, thereby the self-capacitance between them also changes. The self-capacitance refers to the capacitance value between the sensor 13 and the ground unit 14. However, in addition to the proximity of the human body, the change in temperature may also affect the capacitance value, for example, the temperature may cause the dielectric layer 15 and the sensor 13 on the sensing module 11 to expand or contract. The effect of temperature on the capacitance value could be called temperature drift. In practical applications, the effect of temperature drift on the capacitance value even exceeds the change of the capacitance value when the human body approaches. For example, a rapid change in temperature causes the detecting circuit 12 to recognize that the user is wearing a device with such detecting circuit, but in fact the user does not wear the device at this time, or the change in temperature causes the detecting circuit 12 to recognize that the user has removed the device, but in fact the user does not remove the device at this time. Based on this, the prior art has a problem that the capacitance detection is affected by temperature.

SUMMARY

The present application provides a capacitance detection module, a method and an electronic device, thereby avoiding the problem that the capacitance detection is affected by temperature.

In a first aspect, the present application provides a capacitance detection module, including: a sensing module and a detecting circuit; a first sensing unit is disposed on a first surface of the sensing module, and a second sensing unit is disposed on a second surface of the sensing module; the first sensing unit and the second sensing unit are respectively connected to the detecting circuit; and the detecting circuit is configured to determine, according to a capacitance value of the first sensing unit and a capacitance value of the second sensing unit, a wearing state of a device having the capacitance detection module.

In a second aspect, the present application provides a capacitance detection method, the method is applied to a capacitance detection module, and the capacitance detection module includes: a sensing module and a detecting circuit; a sensing module and a detecting circuit; a first sensing unit is disposed on a first surface of the sensing module, and a second sensing unit is disposed on a second surface of the sensing module; the first sensing unit and the second sensing unit are respectively connected to the detecting circuit; and accordingly, the method includes: determining, according to a capacitance value of the first sensing unit and a capacitance value of the second sensing unit, the wearing state of a device having the capacitance detection module.

The present application provides a capacitance detection module, a method, and an electronic device. Since a second sensing unit is added to the capacitance detection module, a first sensing unit and the second sensing unit are simultaneously affected by temperature, but the second sensing unit does not directly touch a human skin, so when a user wears the electronic device with the capacitance detection module, the capacitance value of the first sensing unit reflects influence of temperature and touch of the human skin, and the capacitance value of the second sensing unit only reflects the influence of the temperature, based on this, a wearing state of the device having the capacitance detection module could be determined according to the capacitance values of the first sensing unit and the second sensing unit, that is, the technical solution provided by the embodiment of the present application can avoid a problem that the capacitance detection is affected by temperature.

BRIEF DESCRIPTION OF DRAWINGS

In order to illustrate the embodiments of the present application or the technical solutions in the prior art more clearly, a description of the drawings used in the embodiments or the prior art description will be briefly described below. It is obviously that the drawings described in the following are a certain embodiment of the present application, and other drawings could be obtained according to the drawings without any creative labor for those skilled in the art.

DESCRIPTION OF EMBODIMENTS

The technical solution of the present application is hereinafter described in detail with reference to the accompanying drawings. It is evident that the embodiments are only some exemplary embodiments of the present application, but not all the embodiments. Other embodiments that those skilled in the art obtain based on embodiments of the present application also all within the protection scope of the present application.

The terms "first", "second", and the like (if any) in the specification, claims and the above figures of the present application are used to distinguish similar objects, and are not necessarily used to describe a particular order or a precedence order. It is to be understood that data used in such case may be interchanged as appropriate, such that the embodiments of the present application described herein could be implemented, for example, in a sequence other than those illustrated or described herein. In addition, the terms "includes" and "comprises" and any variations of them are intended to cover a non-exclusive inclusion, for example, a process, method, system, product, or device that comprises a series of steps or units is not necessarily limited to listing these steps or units, but may include other steps or units that not explicitly listed, or that inherent to such processes, methods, products or devices.

Figure 1:
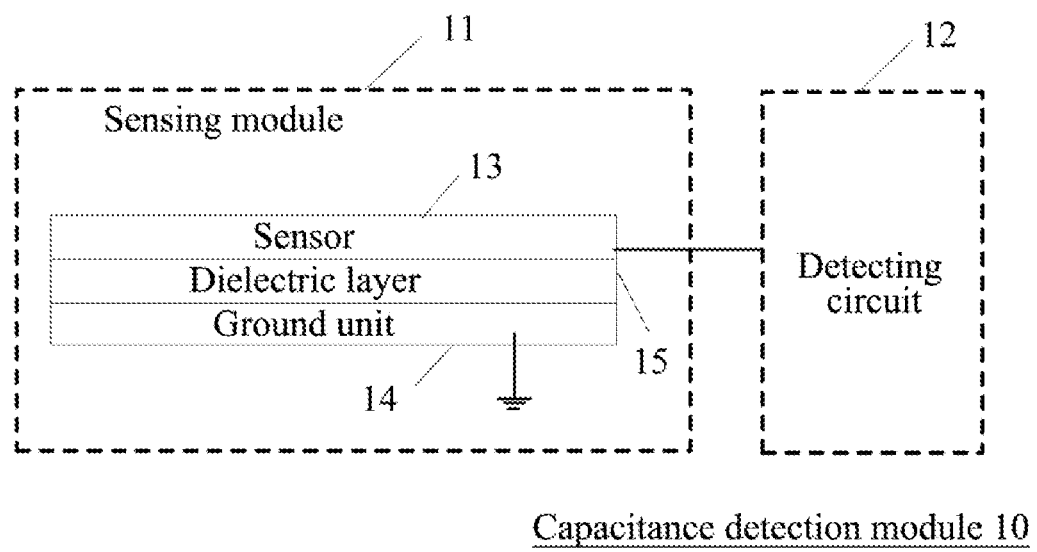
FIG. 1 is a schematic diagram of a capacitance detection module 10 provided by the prior art.
Figure 2:
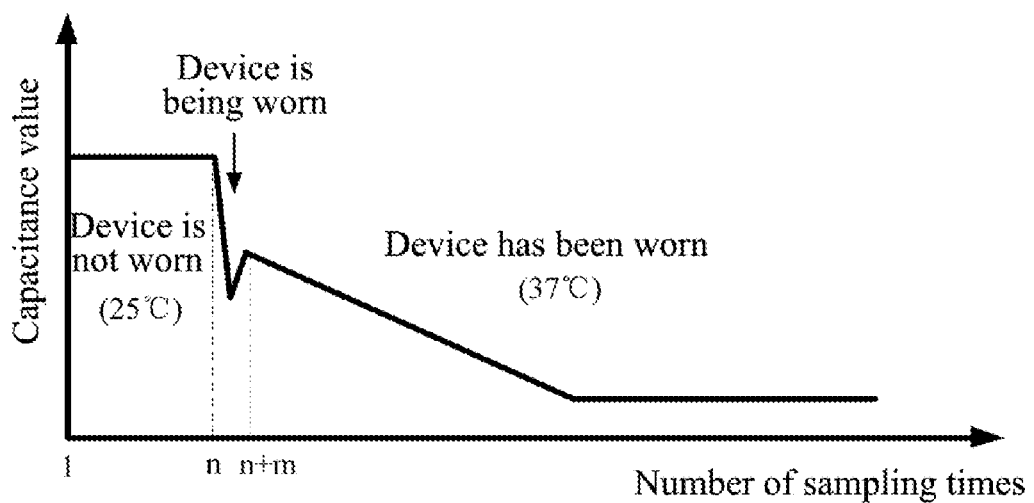
FIG. 2 is a schematic diagram that a capacitance value changes with an influence of wearing and temperature provided by the prior art.

Generally, the capacitance detection module is disposed in an electronic device such as a headphone. FIG. 2 is a schematic diagram that capacitance values changes with wearing and temperature provided by the prior art. As shown in FIG. 2, the abscissa represents the number of sampling times, for example, n indicates the n-th sampling, and the ordinate represents the capacitance value. When a user does not wear the above electronic device, the temperature is at 25 degrees Celsius, since the temperature is stable and the user has not worn the electronic device at this time, the capacitance value is in a stable state; when the user is wearing the electronic device, the capacitance value decreases due to the proximity of the human body and the change of temperature, when the user has worn the electronic device, the capacitance value will first decrease due to the temperature change of temperature from 25 degrees Celsius to 37 degrees Celsius, and when the temperature reaches 37 degrees Celsius, the capacitance value is in a stable state. It should be noted that, assuming that the electronic device is an earphone, when the user is wearing the earphone, the user will first press the earphone to the ear, so the capacitance value first drops to the lowest point, and when the user releases the hand, the earphone will be away from the ear, thus the capacitance value will rise at that moment.

In summary, as mentioned above, an effect of temperature drift on the capacitance value even exceeds the change in capacitance value when the human body approaches in practical applications. For example, a rapid change of temperature causes the detecting circuit to recognize that the user has worn a device having such a detecting circuit, but in fact the user does not wear the device at this time, or the change of temperature causes the detecting circuit to recognize that the user has removed the device, but in fact, the user did not remove the above device at this time. The prior art has a problem that the capacitance detection is affected by temperature. In order to solve the technical problem, the present application provides a capacitance detection module, a method, and an electronic device.

The embodiment of the present application provides a capacitance detection module, including: a sensing module and a detecting circuit; a first sensing unit is disposed on a first surface of the sensing module, and a second sensing unit is disposed on a second surface of the sensing module; the first sensing unit and the second sensing unit are respectively connected to the detecting circuit. The detecting circuit is configured to determine, according to a capacitance value of the first sensing unit and a capacitance value of the second sensing unit, a wearing state of a device having the capacitance detection module.

In an embodiment, the sensing module may be a printed circuit board (PCB), and further, may be a flexible printed circuit board (FPC).

In an embodiment, the first sensing unit is also referred to a sensor or sensing area, and the second sensing unit is also referred to as a sensor or sensing area.

Further, the first surface of the sensing module is a surface that touches with the human body, and the second surface of the sensing module is a surface that does not touch with the human body.

Example I

The first sensing unit is not directly opposite to the second sensing unit; the capacitance of the first sensing unit is a self-capacitance value between the first sensing unit and a ground, and the capacitance of the second sensing unit is a self-capacity value between the second sensing unit and the ground.

Where, it is assumed that the device having the capacitance detection module is horizontally placed, based on this, the so-called "the first sensing unit is not directly opposite to the second sensing unit" means there is a spacing between the first induction unit and the second induction unit in the horizontal direction. Further, the ground may be disposed on the capacitance detection module, for example, may be disposed on the back of the FPC, or may be disposed on a system circuit board that is far away. It is not limited in embodiments of the present application.

The detecting circuit is specifically configured to: collect first reference capacitance between the first sensing unit and the ground, and second reference capacitance between the second sensing unit and the ground, where the first reference capacitance and the second reference capacitance are collected when the device having the capacitance detection module is not worn by the user; then collect first capacitance between the first sensing unit and the ground, and second capacitance between the second sensing unit and the ground, calculate a difference of the first capacitance and the first reference capacitance to obtain first capacitance difference, and calculate a difference of the second capacitance and the second reference capacitance to obtain second capacitance difference; and determine, according to the first capacitance difference and the second capacitance difference, the wearing state of the device having the capacitance detection module.

In an embodiment, the detecting circuit is specifically configured to obtain a capacitance variation of the first sensing unit caused by human skin touch by calculating a product of the second capacitance difference and a preset coefficient and then calculating a difference between the first capacitance difference and the product. The preset coefficient is a ratio of the first capacitance difference to the second capacitance difference when the device is not worn based on a same temperature. Then the wearing state of the user to the device having the capacitance detection module is determined according to the capacitance variation.

Further, the detecting circuit is specifically configured to determine that the device is not worn by user the if the capacitance variation is greater than or equal to a first preset threshold; and determine that the device has been worn by the user if the capacitance variation is smaller than or equal to a second preset threshold; where the second preset threshold is smaller than the first preset threshold.

Specifically, the principle of the Example I is as follows: both the human skin touch and the temperature increase will cause the capacitance value of the sensing unit to change, and the first sensing unit and the second sensing unit are simultaneously affected by temperature, but the human skin does not directly touch the second sensing unit, when the user wears the electronic device, the capacitance variation between the first sensing unit and the ground includes a capacitance variation caused by both the human skin touch and temperature increase, and the capacitance variation between the second sensing unit and the ground includes only the capacitance variation caused by an increase in temperature, and the difference between the two can indicate the capacitance variation caused by human skin touch. The same is true when the user removes the electronic device. Therefore, the wearing state of the user to the device having the capacitance detection module could be determined by the capacitance variation of the first sensing unit caused by touch. Further, the capacitance variation generated by the first sensing unit and the second sensing unit under the influence of the temperature may be referred to as a common mode signal, and the capacitance variation of the first sensing unit and the second sensing unit when touched by human skin may be referred to as a differential mode signal.

Figure 4:
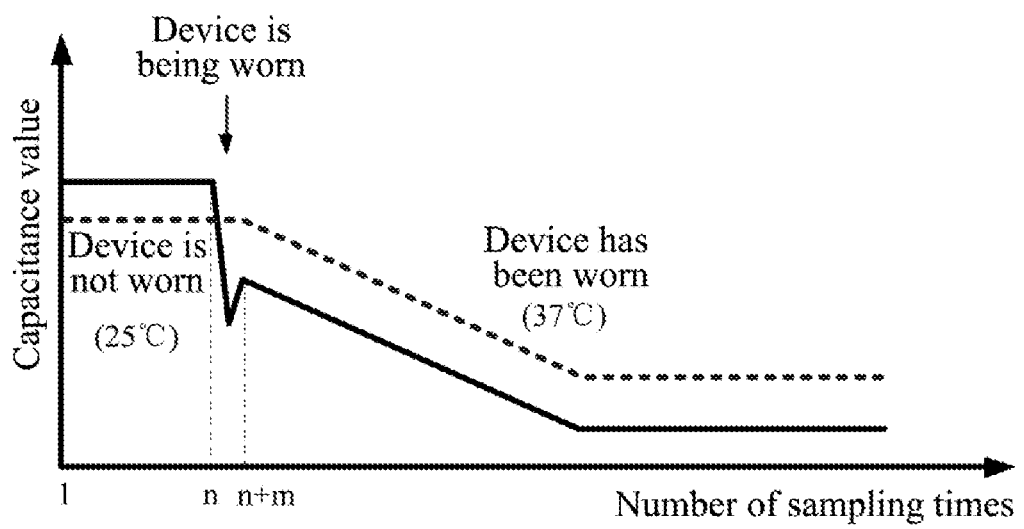
FIG. 4 is a schematic diagram that the capacitance value changes with the influence of the wearing and temperature provided by the present application.

FIG. 4 is a schematic diagram that the capacitance value changes with the influence of the wearing and temperature provided by the present application, and as shown in FIG. 4, the abscissa represents the number of sampling times, for example, n represents the n-th sampling, and the ordinate represents the capacitance value. The solid line indicates the change in capacitance between the first sensing unit and the ground, and the broken line indicates the change in capacitance between the second sensing unit and the ground, and as shown in FIG. 4, when a user does not wear the above-mentioned electronic device, the temperature is at 25 degrees Celsius, since the temperature is stable at this time, and the user has not worn the electronic device, the capacitance value between the first sensing unit and the ground is in a stable state, when the user is wearing the electronic device, the capacitance value decreases due to the proximity of the human body and the change of temperature, and when the user has worn the electronic device, the capacitance value will first decrease due to the temperature change of temperature from 25 degrees Celsius to 37 degrees Celsius, and when the temperature reaches 37 degrees Celsius, the capacitance value is in a stable state. When the user does not wear the above-mentioned electronic device, the temperature is at 25 degrees Celsius, since the temperature is stable and the user has not worn the electronic device at this time, the capacitance value between the second sensing unit and the ground is in a stable state, when the user is wearing the electronic device, since the temperature is still at 25 degrees Celsius and is not affected by human skin touch, so the capacitance value between the second sensing unit and the ground remains stable, and when the user has worn the electronic device, the capacitance value will first decrease due to the temperature change of temperature from 25 degrees Celsius to 37 degrees Celsius, and when the temperature reaches 37 degrees Celsius, the capacitance value is in a stable state.

The following describes the specific calculation manner of the capacitance variation $R_n$ of the first sensing unit caused by touch:

$$R_n = (\text{Sensor}_n - \text{Sensor}_1) - K^*(\text{Ref}_n - \text{Ref}_1)$$

Where, $\text{Sensor}_1$ represents first reference capacitance, $\text{Sensor}_n$ represents first capacitance between the first sensing unit and the ground, $\text{Ref}_1$ represents second reference capacitance, and $\text{Ref}_n$ represents second capacitance between the second sensing unit and the ground, K represents the preset coefficient.

Figure 5:
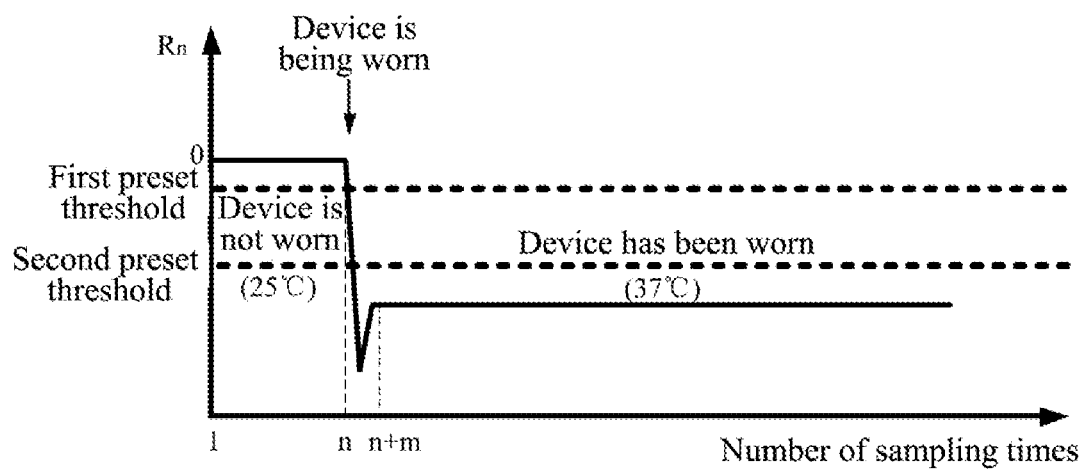
FIG. 5 is a schematic diagram of changes of $R_n$, before and after wearing of the device provided by an embodiment of the present application.

FIG. 5 is a schematic diagram of changes of $R_n$ before and after wearing the device provided by an embodiment of the present application, and as shown in FIG. 5, after the second sensing unit is added, the influence of temperature on capacitance detection is eliminated, and if the capacitance variation $R_n$, is less than or equal to a second preset threshold, it is determined that the device has been worn by a user; at this time, the earphone performs further operations, such as playing music and the like. Accordingly, if the capacitance variation $R_n$, is greater than or equal to a first preset threshold, it is determined that the device is not worn by the user; at this time, the earphone performs further operations, such as pause music and the like. Where, the second preset threshold is smaller than the first preset threshold. If the capacitance variation $R_n$, is between the first preset threshold and the second preset threshold, the judgment is made in conjunction with the wearing state at the previous moment, which is the same as the wearing state at the previous moment.

Example II

Figure 3:
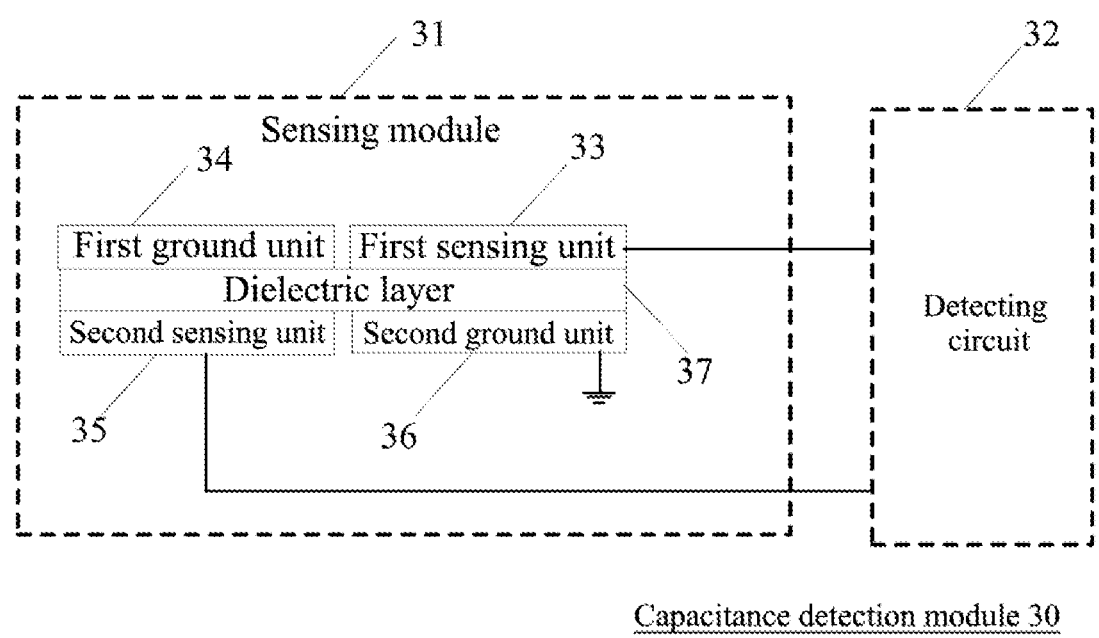
FIG. 3 is a schematic diagram of a capacitance detection module 30 provided by an embodiment of the present application.

FIG. 3 is a schematic diagram of a capacitance detection module 30 provided by an embodiment of the present application, and as shown in FIG. 3, the capacitance detection module 30 includes: a sensing module 31 and a detecting circuit 32; a first sensing unit 33 and a first ground unit 34 are disposed on the first surface of the sensing module 31, and a second sensing unit 35 and a second ground unit 36 are disposed on the second surface of the sensing module 31; where, the first sensing unit 33 is directly opposite to the second ground unit 36, and the second sensing unit 35 is directly opposite to the first ground unit 34. Based on this, the capacitance value of the first sensing unit 33 is a self-capacitance value of the first sensing unit 33 to the second ground unit 36, and the capacitance value of the second sensing unit is a self-capacitance of the second sensing unit 35 to the first ground unit 34. Further, the first sensing unit 33 and the second sensing unit 35 are respectively connected to a detecting circuit 32. In an embodiment, the first sensing unit 33 is also referred to as a sensor or sensing area, and the second sensing unit 35 is also referred to as a sensor or sensing area.

In an embodiment, the first ground unit 34 and the second ground unit 36 are connected to the same ground, which may be understood as two different regions on the sensing module 31.

In an embodiment, a dielectric layer 37 is disposed between the first sensing unit 33 and the second ground unit 36, and the dielectric layer 37 may be a polyimide film or air, and similarly, a dielectric layer 37 is disposed between the second sensing unit 35 and the first ground unit 34, and the dielectric layer 37 may be a polyimide film or air.

The detecting circuit 32 is specifically configured to: collect first reference capacitance of the first sensing unit 33 to the ground, and second reference capacitance of the second sensing unit 35 to the ground; collect first capacitance of the first sensing unit 33 to the ground, and second capacitance of the second sensing unit 35 to the ground, calculate a difference between the first capacitance and the first reference capacitance to obtain first capacitance difference, and calculate a difference between the second capacitance and the second reference capacitance to obtain second capacitance difference; and determine, according to the first capacitance difference and the second capacitance difference, the wearing state of the device having the capacitance detection module.

In an embodiment, the detecting circuit 32 is specifically configured to obtain a capacitance variation of the first sensing unit caused by touch by calculating a product of the second capacitance difference and the preset coefficient and then calculating a difference between the first capacitance difference and the product, the preset coefficient is a ratio of the first capacitance difference to the second capacitance difference when the device is not worn based on a same temperature; and determine, according to the capacitance variation, the wearing state of a user to the device having the capacitance detection module.

Further, the detecting circuit 32 is specifically configured to determine that the device is not worn by user the if the capacitance variation is greater than or equal to a first preset threshold; and determine that the device has been worn by the user if the capacitance variation is smaller than or equal to a second preset threshold; where the second preset threshold is smaller than the first preset threshold. If the capacitance variation is between the first preset threshold and the second preset threshold, it is determined in conjunction with the wearing state of the previous moment, which is the same as the wearing state at the previous moment.

The principle of Example II and the calculation manner of the capacitance variation are the same as those in Example I, which are not described herein again.

Figure 6:
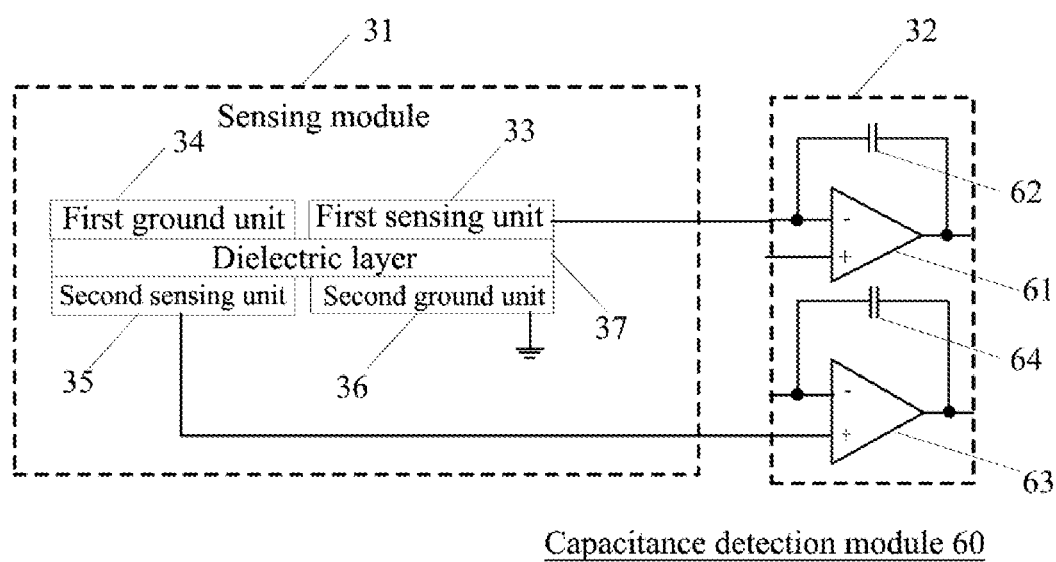
FIG. 6 is a schematic diagram of a capacitance detection module 60 provided by an embodiment of the present application.

In an embodiment, FIG. 6 is a schematic diagram of a capacitance detection module 60 provided by an embodiment of the present application, and as shown in FIG. 6, the detecting circuit 32 includes a first amplifier 61 and a first capacitor 62, and the first capacitor 62 is connected to the first amplifier 61, and the first amplifier 61 is connected to the first sensing unit 33. The capacitance detection module further includes: a second amplifier 63 and a second capacitor 64, the second capacitor 64 is connected to the second amplifier 63, and the second amplifier 63 is connected to the second sensing unit 35.

It should be noted that the structure of the detecting circuit is not limited to that shown in FIG. 6.

Example III

The embodiments of the present application further provide a capacitance detection module, where the first sensing unit is directly opposite to the second sensing unit, and the area of the first sensing unit is the same as the area of the second sensing unit; the capacitance value of the first sensing unit is the self-capacitance value between the first sensing unit and the ground, and the capacitance value of the second sensing unit is the self-capacitance value between the second sensing unit and the ground. The ground may be disposed on the capacitance detection module, for example, may be disposed on the back of the FPC or on the system board that is far away. It is not limited in embodiments of the present application.

In this case, the first sensing unit and the second sensing unit could be simultaneously driven, that is, the first sensing unit and the second sensing unit can maintain the same voltage (0V or driving voltage) at any time, and at this time, since the voltage difference between the two $\Delta U=0$, there is no transfer of charge between the two, both refer to the distant ground, but similarly, because they are affected by temperature similarly, they also have the ability to suppress temperature.

In an embodiment, the first sensing unit is also referred to as a sensor or sensing area, and the second sensing unit is also referred to as a sensor or sensing area.

The detecting circuit is specifically configured to: collect first reference capacitance between the first sensing unit and the ground, and second reference capacitance between the second sensing unit and the ground; collect first capacitance between the first sensing unit and the ground, and second capacitance between the second sensing unit and the ground, calculate a difference between the first capacitance and the first reference capacitance to obtain first capacitance difference, and calculate a difference between the second capacitance and the second reference capacitance to obtain second capacitance difference; and determine, according to the first capacitance difference and the second capacitance difference, the wearing state of the device having the capacitance detection module.

In an embodiment, the detecting circuit is specifically configured to obtain a capacitance variation of the first sensing unit caused by touch by calculating a product of the second capacitance difference and the preset coefficient and then calculating a difference between the first capacitance difference and the product, the preset coefficient is a ratio of the first capacitance difference to the second capacitance difference when the device is not worn based on a same temperature; and determine, according to the capacitance variation, the wearing state of the user to the device having the capacitance detection module.

Further, the detecting circuit is specifically configured to determine that the device is not worn by user the if the capacitance variation is greater than or equal to a first preset threshold; and determine that the device has been worn by the user if the capacitance variation is smaller than or equal to a second preset threshold; where the second preset threshold is smaller than the first preset threshold. If the capacitance variation is between the first preset threshold and the second preset threshold, it is determined in conjunction with the wearing state of the previous moment, which is the same as the wearing state at the previous moment.

The principle of Example III and the calculation manner of the capacitance variation are the same as those in Example I and Example II, which are not described herein again.

In summary, in Example I, Example II or Example III, since a second sensing unit is added to the capacitance detection module, a first sensing unit and the second sensing unit are simultaneously affected by temperature, but the second sensing unit does not directly touch the human skin, so when the user wears the electronic device, the capacitance value of the first sensing unit reflects influence of temperature and touch of the human skin, and the capacitance value of the second sensing unit only reflects the influence of the temperature, based on this, a wearing state of the device having the capacitance detection module could be determined according to the capacitance values of the first sensing unit and the second sensing unit, that is, the technical solution provided by the embodiment of the present application can avoid a problem that the capacitance detection is affected by temperature.

Example IV

Figure 7:
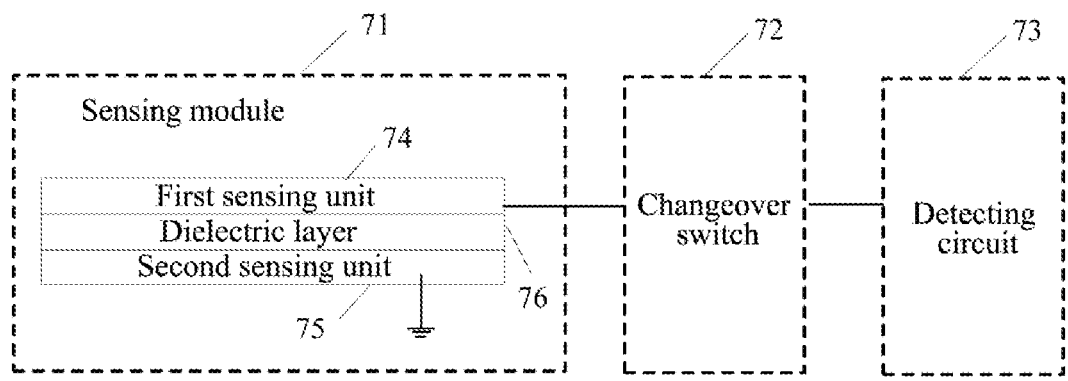
FIG. 7 is a schematic diagram of a capacitance detection module 70 provided by another embodiment of the present application.

FIG. 7 is a schematic diagram of a capacitance detection module 70 provided by another embodiment of the present application, and as shown in FIG. 7, the capacitance detection module 70 includes: a sensing module 71, a changeover switch 72, a detecting circuit 73; a first sensing unit 74 is disposed on a first surface of the sensing module 71, and a second sensing unit 75 is disposed on a second surface of the sensing module 71. Where the first sensing unit 74 is directly opposite to the second sensing unit 75, and the first sensing unit 74 has the same area as the second sensing unit 75. Based on this, the capacitance value of the first sensing unit 74 is the self-capacitance value of the first sensing unit 74 to the second sensing unit 75 which is grounded, and the capacitance value of the second sensing unit 75 is the self-capacitance value of the second sensing unit 75 to the first sensing unit 74 which is grounded.

The changeover switch 72 is configured to perform an alternate switching between a first state and a second state of the state of the sensing module 71. The first state is that the first sensing unit 74 is respectively connected to a driving voltage output by the detecting circuit 73 and a sensing channel of the detecting circuit 73, and the second sensing unit 75 is connected to the ground; the second state is that the second sensing unit 75 is respectively connected to driving voltage output by the detecting circuit 73 and the sensing channel of the detecting circuit 73, the first sensing unit 74 is connected to the ground.

The detecting circuit 73 is specifically configured to: collect first reference capacitance between the first sensing unit 74 and the second sensing unit 75 in the first state, and second reference capacitance between the second sensing unit 75 and the first sensing unit 74 in the second state; collect first capacitance between the first sensing unit 74 and the second sensing unit 75 in the first state, and second capacitance between the second sensing unit 75 and the first sensing unit 74 in the second state, calculate a difference between the first capacitance and the first reference capacitance to obtain first capacitance difference, and calculate a difference between the second capacitance and the second reference capacitance to obtain second capacitance difference; calculate a difference between the first capacitance difference and the second capacitance difference to obtain the capacitance variation of the first sensing unit caused by touch; and determine, according to the capacitance variation, the wearing state of the device having the capacitance detection module.

Further, the detecting circuit 73 is specifically configured to: determine that the device is not worn by user the if the capacitance variation is greater than or equal to a first preset threshold; and determine that the device has been worn by the user if the capacitance variation is smaller than or equal to a second preset threshold; where the second preset threshold is smaller than the first preset threshold. If the capacitance variation is between the first preset threshold and the second preset threshold, it is determined in conjunction with the wearing state of the previous moment, which is the same as the wearing state at the previous moment.

In an embodiment, the sensing module 71 may be a PCB, and further, may be a flexible printed circuit board (FPC).

In an embodiment, the first sensing unit 74 is also referred to as a sensor or sensing area, and the second sensing unit 75 is also referred to as a sensor or sensing area.

In an embodiment, a dielectric layer 76 is disposed between the first sensing unit 74 and the second sensing unit 75, and the dielectric layer 76 may be a polyimide film.

Figure 8:
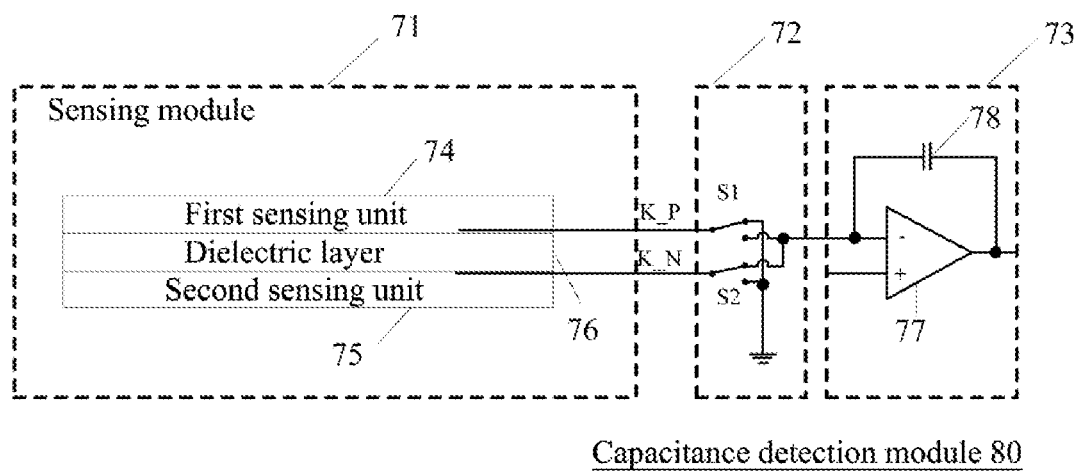
FIG. 8 is a schematic diagram of a capacitance detection module 80 provided by another embodiment of the present application.
Figure 9:
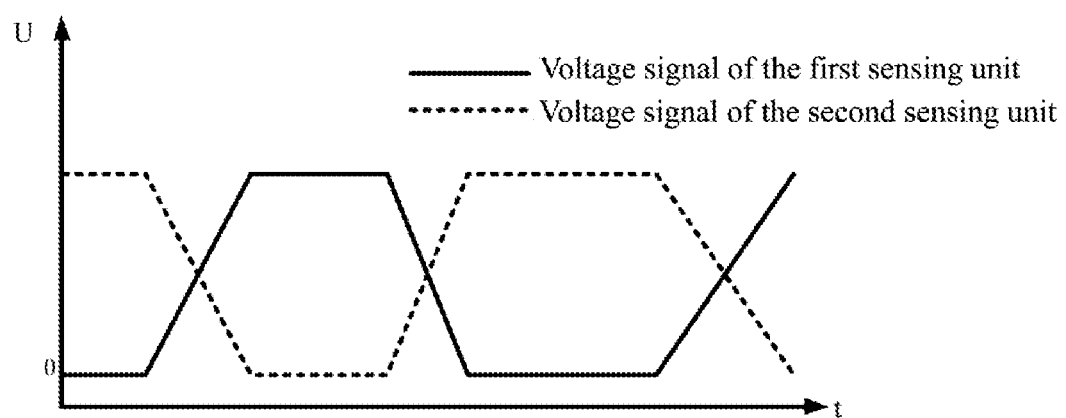
FIG. 9 is a driving timing diagram of a first sensing unit and a second sensing unit.

FIG. 8 is a schematic diagram of a capacitance detection module 80 provided by another embodiment of the present application, and as shown in FIG. 8, the changeover switch 72 is configured to make the first sensing unit 74 and the second sensing unit 75 be alternately driven, and when the first sensing unit 74 is connected to the detecting circuit 73 through the S1 in the changeover switch 72, the first sensing unit 74 is driven, at this time, the second sensing unit 75 is a GND, and when the second sensing unit 75 is connected to the detecting circuit 73 through the S2 in the changeover switch 72, the second sensing unit 75 is driven, and the first sensing unit 74 is a GND. FIG. 9 is a driving timing chart of the first sensing unit and the second sensing unit, and as shown in FIG. 9, the first sensing unit and the second sensing unit are alternately driven.

Further, as shown in FIG. 8, the detecting circuit 73 includes an amplifier 77 and a capacitor 78.

Compared with the technical solution provided in Example I, Example II and Example III, the GND of the technical solution provided in Example IV is dynamic changing, that is, the GND is on the lower surface of the sensing module when the first sensing unit is driven, based on this, the change of capacitance caused by human skin touch and temperature rise when the user wears the device could be sensed, and the GND is on the upper surface of the sensing module when the second sensing unit is driven, and only the change of capacitance caused by the temperature rise when the user wears the device could be sensed. The capacitance variation $R_n$, of the first sensing unit caused by touch is calculated by the following formula.

$$R_n = (\text{Sensor}_n - \text{Sensor}_1) - (\text{Ref}_n - \text{Ref}_1)$$

Where, $\text{Sensor}_1$ represents first reference capacitance, $\text{Sensor}_n$ represents first capacitance between the first sensing unit and the second sensing unit in the first state, and $\text{Ref}_1$ represents second reference capacitance, and $\text{Ref}_n$ represents second capacitance between the first sensing unit and the second sensing unit in the second state.

In summary, in Example IV, the first sensing unit and the second sensing unit are simultaneously affected by temperature, but the second sensing unit does not directly touch human skin, so when the user wears the electronic device, the capacitance variation between the first sensing unit and the second sensing unit in the first state reflects the influence of temperature and the touch of human skin, and the capacitance variation between the second sensing unit and the first sensing unit in the second state only reflects the influence of temperature, therefore, in the embodiments of the present application, the wearing state of the user to the device with capacitance detection module could be determined by the capacitance value of the first sensing unit and the second sensing unit in the first state and the capacitance value of the second sensing unit and the first sensing unit in the second state, that is, the technical solution provided by the embodiments of the present application can avoid the problem that the capacitance detection is affected by temperature.

Example V

The embodiments of the present application further provide a capacitance detection module, where a first sensing unit is directly opposite to a second sensing unit, and the area of the first sensing unit is the same as the area of the second sensing unit, and the capacitance of the first sensing unit is a mutual capacitance value between the first sensing unit and the second sensing unit in a third state, and the capacitance value of the second sensing unit is a mutual capacitance value between the first sensing unit and the second sensing unit in a fourth state; where the third state is that the first sensing unit is connected to a driving voltage output by the detecting circuit, and the second sensing unit is connected to a sensing channel of the detecting circuit; where the fourth state is that the second sensing unit is connected to the driving voltage output by the detecting circuit, and the first sensing unit is connected to the sensing channel of the detecting circuit.

The detecting circuit further includes a changeover switch, and the switching switch is configured to perform an alternate switching between the third state and the fourth state of the state of the sensing module;

The detecting circuit is specifically configured to: collect first reference capacitance between the first sensing unit and the second sensing unit in the third state, and second reference capacitance between the second sensing unit and the first sensing unit in the second state; collect first capacitance between the first sensing unit and the second sensing unit in the fourth state, and second capacitance between the second sensing unit and the first sensing unit in the second state, calculate a difference between the first capacitance and the first reference capacitance to obtain first capacitance difference, and calculate a difference between the second capacitance and the second reference capacitance to obtain second capacitance difference; calculate a difference between the first capacitance difference and the second capacitance difference to obtain a capacitance variation touch of the first sensing unit caused by touch; and determine, according to the capacitance variation, the wearing state of the device having the capacitance detection module.

In an embodiment, the detecting circuit is specifically configured to: determine that the device is not worn by user the if the capacitance variation is greater than or equal to a first preset threshold; and determine that the device has been worn by the user if the capacitance variation is smaller than or equal to a second preset threshold; where the second preset threshold is smaller than the first preset threshold. If the capacitance variation is between the first preset threshold and the second preset threshold, it is determined in conjunction with the wearing state of the previous moment, which is the same as the wearing state at the previous moment.

In an embodiment, the sensing module may be a PCB, and further, may be a flexible printed circuit board (FPC).

In an embodiment, the first sensing unit is also referred to as a sensor or sensing area, and the second sensing unit is also referred to as a sensor or sensing area.

In an embodiment, a dielectric layer is disposed between the first sensing unit and the second sensing unit, and the dielectric layer may be a polyimide film.

The capacitance variation $R_n$ of the first sensing unit caused by touch is calculated by the following formula.

$$R_n = (Sensor_n - Sensor_1) - (Ref_n - Ref_1)$$

Where, $Sensor_1$ represents first reference capacitance, and $Sensor_n$ represents first capacitance between the first sensing unit and the second sensing unit in the third state, and $Ref_1$ represents the second reference capacitance, and $Ref_n$ represents second capacitance between the first sensing unit and the second sensing unit in the fourth state.

In summary, in Example V, the first sensing unit and the second sensing unit are simultaneously affected by temperature, but the second sensing unit does not directly touch human skin, so when the user wears the electronic device, the capacitance variation between the first sensing unit and the second sensing unit in the third state reflects the influence of temperature and the touch of human skin, and the capacitance variation between the first sensing unit and the second sensing unit in the fourth state only reflects the influence of temperature, therefore, in the embodiments of the present application, the wearing state of the user to the device having the capacitance detection module could be determined by the capacitance value of the first sensing unit and the second sensing unit in the third state and the capacitance value of the second sensing unit and the first sensing unit in the fourth state, that is, the technical solution provided by the embodiments of the present application can avoid the problem that the capacitance detection is affected by temperature.

A capacitance detection method is provided by an embodiment of the present application, the method is applied to a capacitance detection module, which includes a sensing module and a detecting circuit; a first sensing unit is disposed on the first surface of the sensing module, and a second sensing unit is disposed on a second surface of the second sensing module; the first sensing unit and the second sensing unit are respectively connected to the detecting circuit; the capacitance value of the first sensing unit is a self-capacitance value between the first sensing unit and the ground, and the capacitance value of the second sensing unit is the self-capacitance value between the second sensing unit and the ground. Accordingly, the method includes: the detecting circuit determines the wearing state of the user to the device having the capacitance detection module according to the capacitance value of the first sensing unit and the capacitance value of the second sensing unit.

Figure 10:
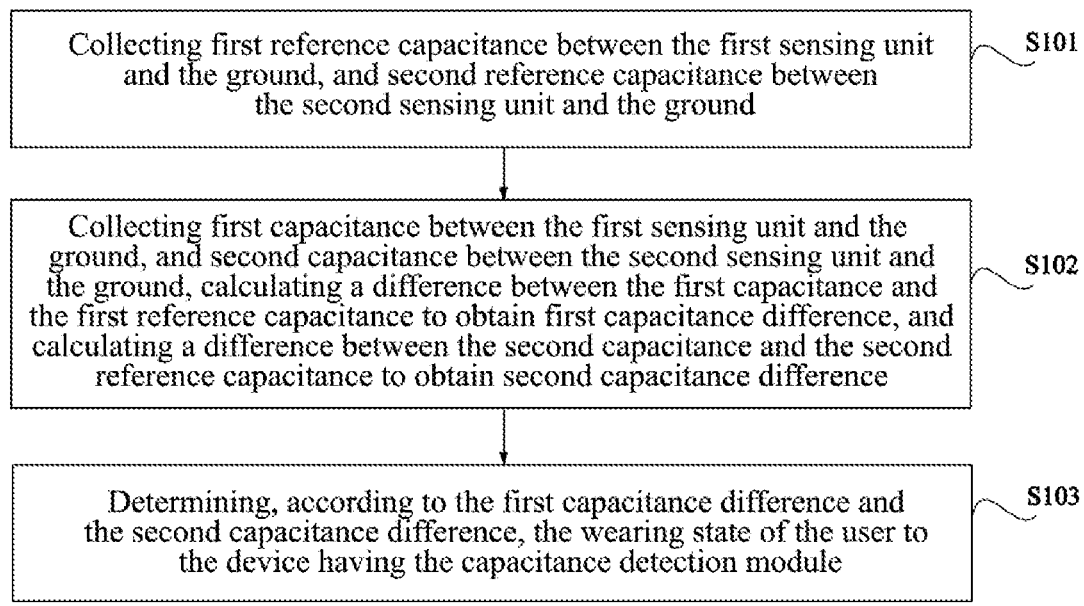
FIG. 10 is a flowchart of a capacitance detection method provided by an embodiment of the present application.

Optional Method I:

FIG. 10 is a flowchart of a capacitance detection method provided by an embodiment of the present application, which is based on the above-mentioned capacitance detection module provided by Example I, Example II or Example III, accordingly, as shown in FIG. 10, the detecting circuit determines the wearing state of a user to the device having the capacitance detection module according to the capacitance value of the first sensing unit and the capacitance value of the second sensing unit, includes the following steps:

Step S101: collecting first reference capacitance between the first sensing unit and the ground, and second reference capacitance between the second sensing unit and the ground.

Step S102: collecting first capacitance between the first sensing unit and the ground, and second capacitance between the second sensing unit and the ground, calculating a difference between the first capacitance and the first reference capacitance to obtain first capacitance difference, and calculating a difference between the second capacitance and the second reference capacitance to obtain second capacitance difference.

Step S103: determining, according to the first capacitance difference and the second capacitance difference, the wearing state of the user to the device having the capacitance detection module.

Figure 11:
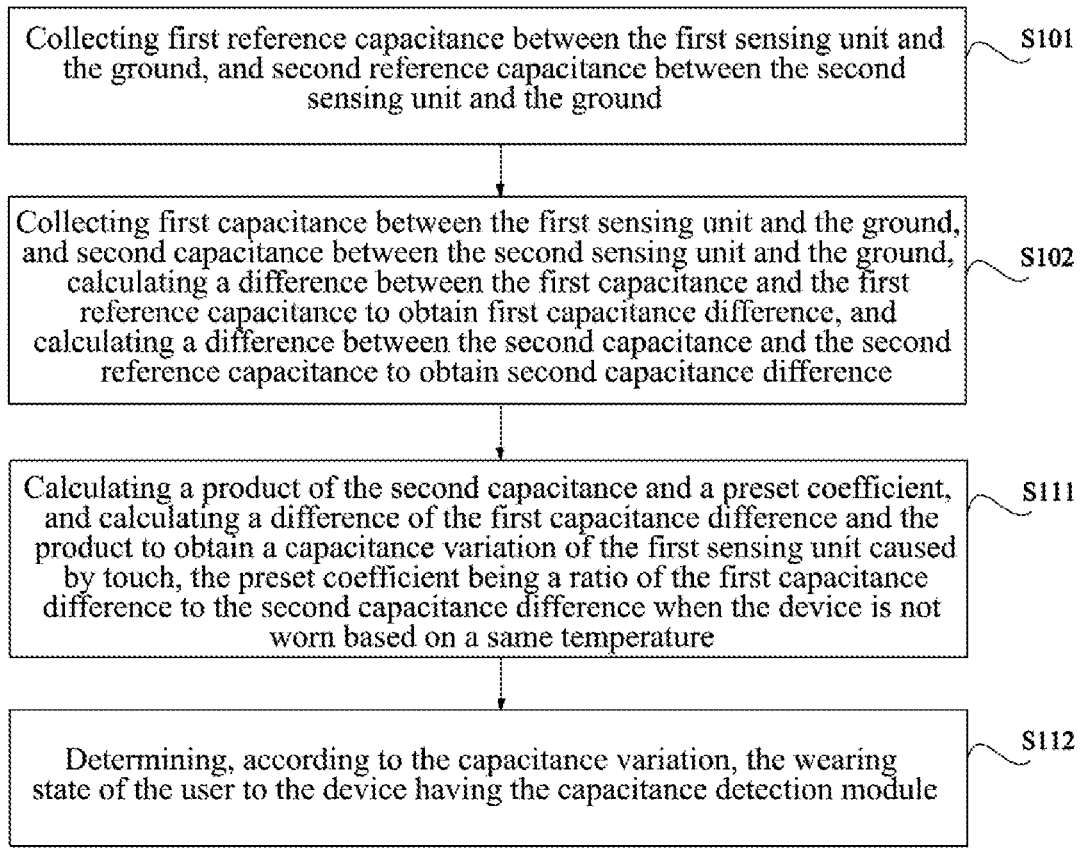
FIG. 11 is a flowchart of a capacitance detection method provided by another embodiment of the present application.

In an embodiment, FIG. 11 is a flowchart of a capacitance detection method provided by another embodiment of the present application, and as shown in FIG. 11, the step S103 includes the following steps:

Step S111: calculating a product of the second capacitance difference and the preset coefficient, and calculating a difference between the first capacitance difference and the product to obtain a capacitance variation of the first sensing unit caused by touch, where the preset coefficient being a ratio of the first capacitance difference to the second capacitance difference when the device is not worn based on a same temperature.

Step S112: determine, according to the capacitance variation, the wearing state of the user to the device having the capacitance detection module.

Where, if the capacitance variation is greater than or equal to a first preset threshold, determining that the device is not worn by the user; if the capacitance variation is less than or equal to a second preset threshold, determining that the device has been worn by the user; where the second preset threshold is less than the first preset threshold. If the capacitance variation is between the first preset threshold and the second preset threshold, it is determined in conjunction with the wearing state of the previous moment, which is the same as the wearing state at the previous moment.

The capacitance detection method provided by the embodiments of the present application may be executed by the capacitance detection module of Example I, Example II, or Example III, the content and effect thereof may refer to Example I, Example II, or Example III, which are not described herein again.

Figure 12:
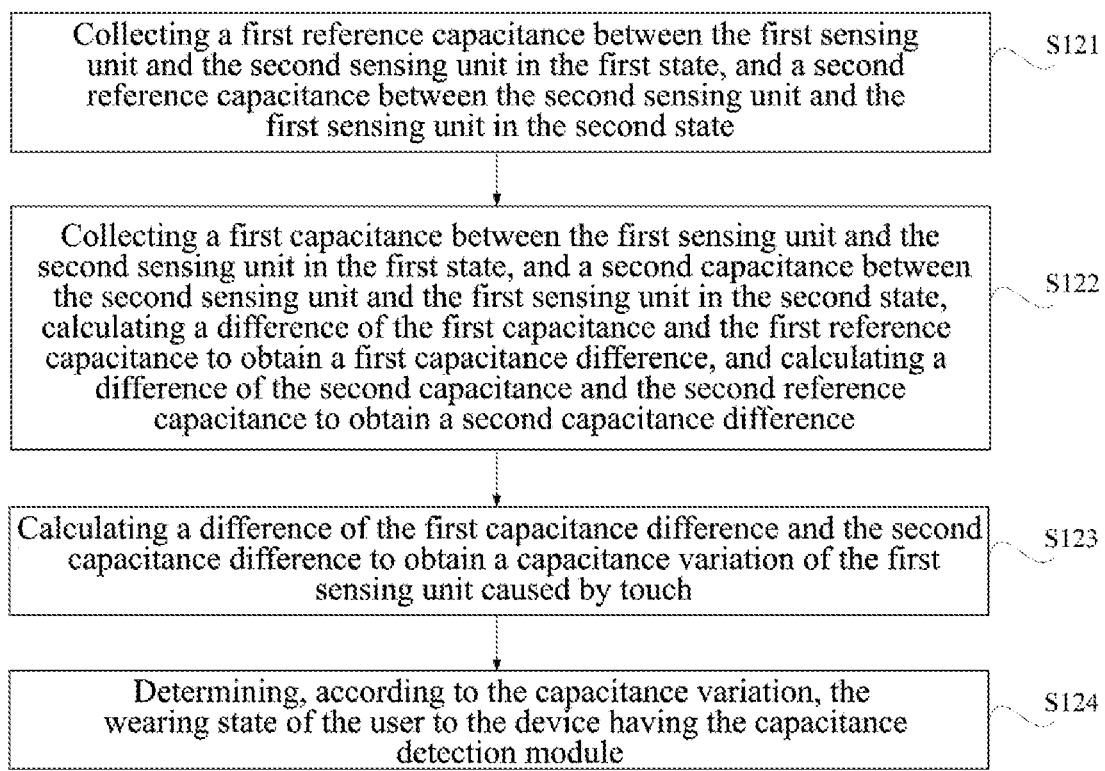
FIG. 12 is a flowchart of a capacitance detection method provided by an embodiment of the present application.

FIG. 12 is a flowchart of a capacitance detection method provided by an embodiment of the present application, the method is applied to the capacitance detection module provided in Example IV, and accordingly, as shown in FIG. 12, the detecting circuit determines the wearing state of the user to the device having the capacitance detection module according to the capacitance value of the first sensing unit and the capacitance value of the second sensing unit, includes the following steps:

Step S121: collecting first reference capacitance between the first sensing unit and the second sensing unit in the first state, and second reference capacitance between the second sensing unit and the first sensing unit in the second state.

Step S122: collecting first capacitance between the first sensing unit and the second sensing unit in the first state, and second capacitance between the second sensing unit and the first sensing unit in the second state, calculating a difference between the first capacitance and the first reference capacitance to obtain first capacitance difference, and calculating a difference between the second capacitance and the second reference capacitance to obtain second capacitance difference.

Step S123: calculating a difference between the first capacitance difference and the second capacitance difference to obtain a capacitance variation of the first sensing unit caused by touch.

Step S124: determining, according to the capacitance variation, the wearing state of the user to the device having the capacitance detection module.

Where, if the capacitance variation is greater than or equal to a first preset threshold, determining that the device is not worn by the user; if the capacitance variation is less than or equal to a second preset threshold, determining that the device has been worn by the user; where the second preset threshold is less than the first preset threshold.

The capacitance detection method provided by the embodiments of the present application may be executed by the capacitance detection module of Example IV, the content and effect thereof may refer to Example IV, which are not described herein again.

Figure 13:
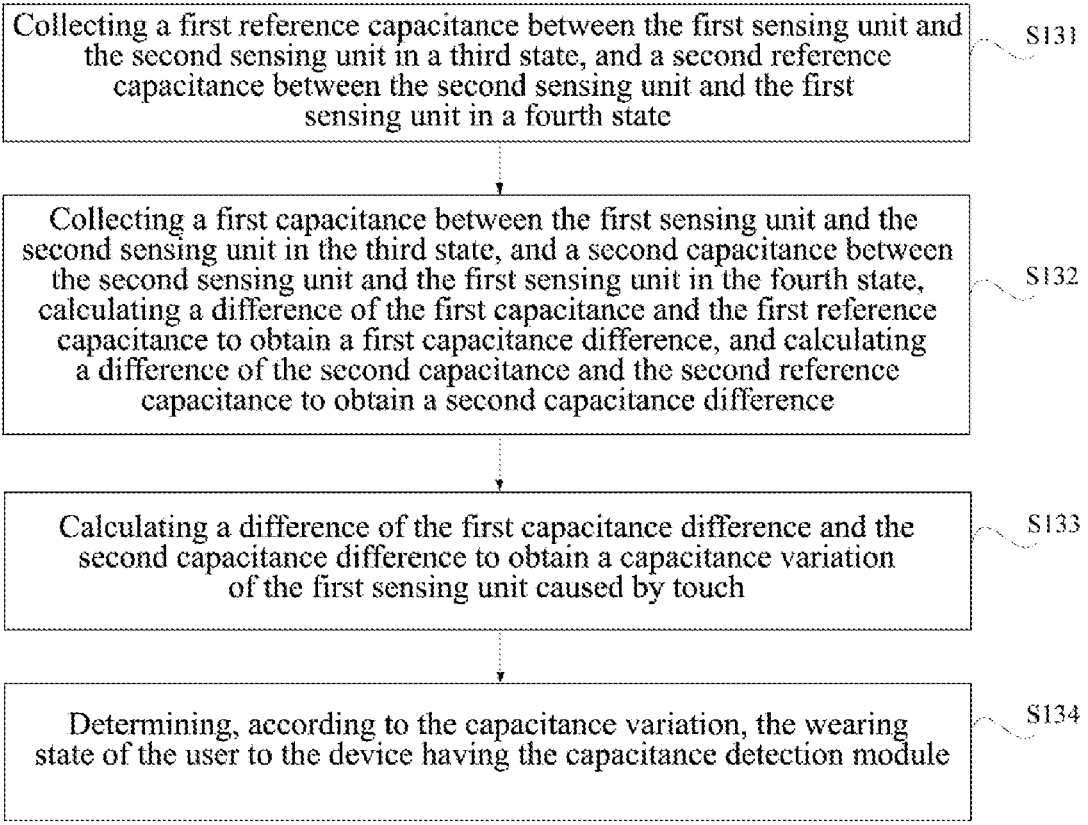
FIG. 13 is a flowchart of a capacitance detection method provided by another embodiment of the present application.

FIG. 13 is a flowchart of a capacitance detection method provided by another embodiment of the present application, the method is applied to the capacitance detection module provided in Example V, and accordingly, as shown in FIG. 13, the detecting circuit determines the wearing state of a user to the device having the capacitance detection module according to the capacitance value of the first sensing unit and the capacitance value of the second sensing unit, includes the following steps:

Step S131: collecting first reference capacitance between the first sensing unit and the second sensing unit in the third state, and second reference capacitance between the second sensing unit and the first sensing unit in the fourth state;

Step S132: collecting first capacitance between the first sensing unit and the second sensing unit in the third state, and second capacitance between the second sensing unit and the first sensing unit in the fourth state, calculating a difference between the first capacitance and the first reference capacitance to obtain first capacitance difference, and calculating a difference between the second capacitance and the second reference capacitance to obtain second capacitance difference;

Step S133: calculating a difference between the first capacitance difference and the second capacitance difference to obtain a capacitance variation of the first sensing unit caused by touch.

Step S134: determining, according to the capacitance variation, the wearing state of the user to the device having the capacitance detection module.

The capacitance detection method provided in the embodiments of the present application may be executed by the capacitance detection module of Example V, the content and effect thereof may refer to the Example V, which are not described herein again.

The present application further provides an electronic device, the electronic device includes the capacitance detection module of Example I, Example II, Example III, Example IV, or Example V. In an embodiment, the electronic device may be an earphone.

Since the electronic device provided by the embodiments of the present application includes Example I, Example II, Example III, Example IV, or Example V, and the content and effect thereof may refer to Example I, Example II, Example III, Example IV, or Example V, which are not described herein again.

What is claimed is:

1. A capacitance detection module, comprising: a sensing module and a detecting circuit; a first sensing unit is disposed on a first surface of the sensing module, and a second sensing unit is disposed on a second surface of the sensing module; the first sensing unit and the second sensing unit are respectively connected to the detecting circuit;

the detecting circuit is configured to determine, according to a capacitance value of the first sensing unit and a capacitance value of the second sensing unit, a wearing state of a device having the capacitance detection module;

wherein the first sensing unit is directly opposite to the second sensing unit, and the area of the first sensing unit is the same as the area of the second sensing unit; the capacitance value of the first sensing unit is a self-capacitance value between the first sensing unit and the second sensing unit which is grounded, the capacitance value of the second sensing unit is a self-capacitance value between the second sensing unit and the first sensing unit which is grounded; wherein the detecting circuit further comprises a changeover switch, wherein the changeover switch is configured to perform an alternate switching between a first state and a second state of the state of the sensing module, wherein the first state is that the first sensing unit is respectively connected to a driving voltage output by the detecting circuit and a sensing channel of the detecting circuit, and the second sensing unit is connected to the ground; wherein the second state is that the second sensing unit is respectively connected to the driving voltage output by the detecting circuit and the sensing channel of the detecting circuit, and the first sensing unit is connected to the ground; and the detecting circuit is configured to: collect first reference capacitance between the first sensing unit and the second sensing unit in the first state, and second reference capacitance between the second sensing unit and the first sensing unit in the second state; collect first capacitance between the first sensing unit and the second sensing unit in the first state, and second capacitance between the second sensing unit and the first sensing unit in the second state, calculate a difference of the first capacitance and the first reference capacitance to obtain first capacitance difference, and calculate a difference of the second capacitance and the second reference capacitance to obtain second capacitance difference; calculate a difference of the first capacitance difference and the second capacitance difference to obtain a capacitance variation of the first sensing unit caused by touch; determine, according to the capacitance variation, the wearing state of the device having the capacitance detection module;

or, wherein the first sensing unit is directly opposite to the second sensing unit, and the area of the first sensing unit is the same as the area of the second sensing unit, the capacitance value of the first sensing unit is a mutual capacitance value between the first sensing unit and the second sensing unit, and the capacitance value of the second sensing unit is a mutual capacitance value between the second sensing unit and the first sensing unit wherein the detecting circuit further comprises a changeover switch, wherein the changeover switch is configured to perform an alternate switching between a third state and a fourth state of the state of the sensing module; wherein the third state is that the first sensing unit is connected to a driving voltage output by the detecting circuit, and the second sensing unit is connected to a sensing channel of the detecting circuit wherein the fourth state is that the second sensing unit is connected to the driving voltage output by the detecting circuit, and the first sensing unit is connected to the sensing channel of the detecting circuit and the detecting circuit is configured to: collect first reference capacitance between the first sensing unit and the second sensing unit in the third state, and second reference capacitance between the second sensing unit and the first sensing unit in the fourth state; collect first capacitance between the first sensing unit and the second sensing unit in the third state, and second capacitance between the second sensing unit and the first sensing unit in the fourth state, calculate a difference of the first capacitance and the first reference capacitance to obtain first capacitance difference, and calculate a difference of the second capacitance and the second reference capacitance to obtain second capacitance difference; calculate a difference of the first capacitance difference and the second capacitance difference to obtain a capacitance variation of the first sensing unit caused by touch; determine, according to the capacitance variation, the wearing state of the device having the capacitance detection module.

2. The module according to claim 1, wherein the detecting circuit is configured to:
determine that the device is not worn if the capacitance variation is greater than or equal to a first preset threshold;
determine that the device has been worn if the capacitance variation is smaller than or equal to a second preset threshold;
wherein the second preset threshold is smaller than the first preset threshold.

3. A capacitance detection method, wherein the method is applied in a capacitance detection module, the capacitance detection module comprising: a sensing module and a detecting circuit; a first sensing unit is disposed on a first surface of the sensing module, and a second sensing unit is disposed on a second surface of the sensing module; the first sensing unit and the second sensing unit are respectively connected to the detecting circuit;

accordingly, the method comprises:
determining, according to a capacitance value of the first sensing unit and a capacitance value of the second sensing unit, the wearing state of a device having the capacitance detection module;
wherein the first sensing unit is directly opposite to the second sensing unit, and the area of the first sensing unit is the same as the area of the second sensing unit the capacitance value of the first sensing unit is a self-capacitance value between the first sensing unit and the second sensing unit which is grounded, and the capacitance value of the second sensing unit is a self-capacitance between the second sensing unit and the first sensing unit which is grounded; the detecting circuit further comprises a changeover switch, wherein the changeover switch is configured to perform an alternate switching between a first state and a second state of the state of the sensing module, wherein the first state is that the first sensing unit is respectively connected to a driving voltage output by the detecting circuit and a sensing channel of the detecting circuit, and the second sensing unit is connected to the ground; wherein the second state is that the second sensing unit is connected to the driving voltage output by the detecting circuit and the sensing channel of the detecting circuit, and the first sensing unit being connected to the ground; accordingly, the determining, according to a capacitance value of the first sensing unit and a capacitance value of the second sensing unit, the wearing state of a device having the capacitance detection module, comprises: collecting first reference capacitance between the first sensing unit and the second sensing unit in the first state, and second reference capacitance between the second sensing unit and the first sensing unit in the second state; collecting first capacitance between the first sensing unit and the second sensing unit in the first state, and second capacitance between the second sensing unit and the first sensing unit in the second state, calculating a difference of the first capacitance and the first reference capacitance to obtain first capacitance difference, and calculating a difference of the second capacitance and the second reference capacitance to obtain second capacitance difference; calculating a difference of the first capacitance difference and the second capacitance difference to obtain a capacitance variation of the first sensing unit caused by touch; determining, according to the capacitance variation, the wearing state of the device having the capacitance detection module;

or, wherein the first sensing unit is directly opposite to the second sensing unit, and the area of the first sensing unit is the same as the area of the second sensing unit, the capacitance value of the first sensing unit is a mutual capacitance value between the first sensing unit and the second sensing unit, and the capacitance value of the second sensing unit is a mutual capacitance value between the second sensing unit and the first sensing unit the detecting circuit further comprises a changeover switch, wherein the changeover switch is configured to perform an alternate switching between a third state and a fourth state of the state of the sensing module; wherein the third state is that the first sensing unit is connected to a driving voltage output by the detecting circuit, and the second sensing unit is connected to a sensing channel of the detecting circuit; wherein the fourth state is that the second sensing unit is connected to the driving voltage output by the detecting circuit, and the first sensing unit is connected to the sensing channel of the detecting circuit accordingly, the determining, according to a capacitance value of the first sensing unit and a capacitance value of the second sensing unit, the wearing state of a device having the capacitance detection module, comprises: collecting first reference capacitance between the first sensing unit and the second sensing unit in the third state, and second reference capacitance between the second sensing unit and the first sensing unit in the fourth state; collecting first capacitance between the first sensing unit and the second sensing unit in the third state, and second capacitance between the second sensing unit and the first sensing unit in the fourth state, calculating a difference of the first capacitance and the first reference capacitance to obtain first capacitance difference, and calculating a difference of the second capacitance and the second reference capacitance to obtain second capacitance difference; calculating a difference of the first capacitance difference and the second capacitance difference to obtain a capacitance variation of the first sensing unit caused by touch; determining, according to the capacitance variation, the wearing state of the device having the capacitance detection module.

4. The method according to claim 3, wherein the determining, according to the capacitance variation, the wearing state of the device having the capacitance detection module, comprises:

determining that the device is not worn if the capacitance variation is greater than or equal to a first preset threshold;

determining that the device has been worn if the capacitance variation is smaller than or equal to a second preset threshold;

wherein the second preset threshold is smaller than the first preset threshold.

5. An electronic device, comprising a capacitance detection module, wherein the capacitance detection module comprises a sensing module and a detecting circuit, a first sensing unit is disposed on a first surface of the sensing module, and a second sensing unit is disposed on a second surface of the sensing module; the first sensing unit and the second sensing unit are respectively connected to the detecting circuit;

the detecting circuit is configured to determine, according to a capacitance value of the first sensing unit and a capacitance value of the second sensing unit, a wearing state of the electronic device;

wherein the first sensing unit is directly opposite to the second sensing unit, and the area of the first sensing unit is the same as the area of the second sensing unit; the capacitance value of the first sensing unit is a self-capacitance value between the first sensing unit and the second sensing unit which is grounded, the capacitance value of the second sensing unit is a self-capacitance value between the second sensing unit and the first sensing unit which is grounded; wherein the detecting circuit further comprises a changeover switch, wherein the changeover switch is configured to perform an alternate switching between a first state and a second state of the state of the sensing module, wherein the first state is that the first sensing unit is respectively connected to a driving voltage output by the detecting circuit and a sensing channel of the detecting circuit, and the second sensing unit is connected to the ground; wherein the second state is that the second sensing unit is respectively connected to the driving voltage output by the detecting circuit and the sensing channel of the detecting circuit, and the first sensing unit is connected to the ground; and the detecting circuit is configured to: collect first reference capacitance between the first sensing unit and the second sensing unit in the first state, and second reference capacitance between the second sensing unit and the first sensing unit in the second state; collect first capacitance between the first sensing unit and the second sensing unit in the first state, and second capacitance between the second sensing unit and the first sensing unit in the second state, calculate a difference of the first capacitance and the first reference capacitance to obtain first capacitance difference, and calculate a difference of the second capacitance and the second reference capacitance to obtain second capacitance difference; calculate a difference of the first capacitance difference and the second capacitance difference to obtain a capacitance variation of the first sensing unit caused by touch; determine, according to the capacitance variation, the wearing state of the electronic device;

or, wherein the first sensing unit is directly opposite to the second sensing unit, and the area of the first sensing unit is the same as the area of the second sensing unit, the capacitance value of the first sensing unit is a mutual capacitance value between the first sensing unit and the second sensing unit, and the capacitance value of the second sensing unit is a mutual capacitance value between the second sensing unit and the first sensing unit wherein the detecting circuit further comprises a changeover switch, wherein the changeover switch is configured to perform an alternate switching between a third state and a fourth state of the state of the sensing module; wherein the third state is that the first sensing unit is connected to a driving voltage output by the detecting circuit, and the second sensing unit is connected to a sensing channel of the detecting circuit wherein the fourth state is that the second sensing unit is connected to the driving voltage output by the detecting circuit, and the first sensing unit is connected to the sensing channel of the detecting circuit and the detecting circuit is configured to: collect first reference capacitance between the first sensing unit and the second sensing unit in the third state, and second reference capacitance between the second sensing unit and the first sensing unit in the fourth state; collect first capacitance between the first sensing unit and the second sensing unit in the third state, and second capacitance between the second sensing unit and the first sensing unit in the fourth state, calculate a difference of the first capacitance and the first reference capacitance to obtain first capacitance difference, and calculate a difference of the second capacitance and the second reference capacitance to obtain second capacitance difference; calculate a difference of the first capacitance difference and the second capacitance difference to obtain a capacitance variation of the first sensing unit caused by touch; determine, according to the capacitance variation, the wearing state of the electronic device.

6. The electronic device according to claim 5, wherein the detecting circuit is configured to:
    determine that the device is not worn if the capacitance variation is greater than or equal to a first preset threshold;
    determine that the device has been worn if the capacitance variation is smaller than or equal to a second preset threshold;
    wherein the second preset threshold is smaller than the first preset threshold.

* * * * *